(12) United States Patent
McCauley et al.

(10) Patent No.: US 8,371,152 B2
(45) Date of Patent: Feb. 12, 2013

(54) HELIUM CONSERVATION DEVICE FOR A GAS CHROMATOGRAPH

(75) Inventors: Edward B. McCauley, Cedar Park, TX (US); Paolo Magni, Izano (IT)

(73) Assignee: Thermo Finnigan LLC, San Jose, CA (US)

( * ) Notice: Subject to any disclaimer, the term of this patent is extended or adjusted under 35 U.S.C. 154(b) by 288 days.

(21) Appl. No.: 12/913,653

(22) Filed: Oct. 27, 2010

(65) Prior Publication Data

US 2012/0103064 A1 May 3, 2012

(51) Int. Cl.
*B01D 53/02* (2006.01)
(52) U.S. Cl. ...................................... 73/23.22; 73/23.23
(58) Field of Classification Search .................. 73/23.22, 73/23.23
See application file for complete search history.

(56) References Cited

PUBLICATIONS

Harry Prest, "Reducing Helium Costs more than 10-fold with the PCT Gas Saver mode," Technical Overview, Agilent Technologies, pp. 1-9, (2010).

*Primary Examiner* — Lisa Caputo
*Assistant Examiner* — Punam Roy
(74) *Attorney, Agent, or Firm* — Pamela Lau Kee

(57) ABSTRACT

A device for conserving helium gas in a gas chromatograph system is characterized in that during the majority of an analytical separation, helium is used as the carrier gas while an auxiliary non-helium gas is used to pressurize the inlet and provide for septum purge and split vent flow. Prior an injection period, a coaxial helium flow is established at the column entrance wherein the coaxial helium flow is less than the column flow. Following the injection and sample transfer period, a coaxial helium flow is established wherein the flow is greater than the column flow.

14 Claims, 7 Drawing Sheets

HELIUM CONSERVATION DEVICE FOR A GAS CHROMATOGRAPH

BACKGROUND

Traditional split/splitless (SSL) or programmed temperature vaporizing (PTV) injection ports for gas chromatographs typically consume large volumes of carrier gas by virtue of what is used at the split vent and septum purge vent rather than what is utilized for the actual analytical separation (column flow). To illustrate, a capillary column flow of approximately 1 standard cubic centimeter per minute (sccm) may have 50 sccm or more of split flow and 5 sccm of septum purge flow. One prior art method to reduce this consumption, e.g. "gas saver", can reduce the split flow following an injection period. Reducing the split flow to too low a value however can result in undesirable elevated baselines. This may be caused by a continual outgassing of higher molecular weight contaminants introduced from the sample matrix, outgassing of polymeric seals such as O-rings, injection port septa and/or coring of such septa, or be caused by oxidation of the column stationary phase due to larger concentrations of oxygen which has back-diffused through the septum. Reducing these contaminants has traditionally been accomplished through dilution by using large split flows.

FIG. 1 illustrates a typical gas chromatograph inlet system of the prior art. The system includes a split/splitless (SSL) injector for injecting liquid samples. A carrier gas is delivered via an electronic pressure controller to the injector. A gas supply, e.g. helium, is introduced under pressure to a gas fitting. A fine porosity filter, e.g. a stainless steel frit, removes any particulate matter that may foul operation of the proportional valve. The proportional valve maintains a setpoint pressure within the body of the injector to establish a calculated flow in the analytical column. The proportional valve can be controlled by sensing the pressure of the injector using a pressure sensor that provides a feedback loop to the control circuit (not shown). Optionally, a chemical trap is included to scrub the carrier gas of potential contaminants, e.g. hydrocarbons and/or oxygen. Additional proportional valves allow purging and venting of some of the delivered carrier gas from the septum purge vent and split vent respectively, by calculation of the pressure drop across restrictors.

FIG. 2 illustrates a detailed example of a prior art SSL injector shown in FIG. 1. A septum, held in place by a septum nut, is pierced by the needle of a small syringe (not shown) to allow liquid to be flash vaporized within the inlet liner. The temperature of a heater block is regulated by a heater assembly (not shown). A supply of gas entering the injector assembly establishes a flow in the capillary column. There are two modes of operation: split and splitless.

In the split injection mode, a split flow is established that exits the split line. The flow exiting the split line is controlled by the electronic pressure controller of FIG. 1. This mode is used for injection of concentrated analytes to prevent overloading of the column or saturation of the detection system used at the terminal end of the column.

In the splitless mode of operation, the split line is closed during injection to cause the bulk of the sample material to be transferred to the capillary column. After a specified time interval, the split vent is opened to vent residual solvent vapors and to dilute any contaminants that might outgas from contaminated surfaces.

In both modes, far greater amounts of carrier gas are used for split flow and septum purge flow than are required for the gas chromatography (GC) column flow carrying out the analytical separation. Following a split or splitless injection, large volumes of split flow are typically maintained to dilute outgassing of residual contaminants. This results in a large consumption of high purity gas, e.g. helium.

Helium is becoming increasingly expensive and difficult to procure in some areas of the world. Helium is often the preferred gas of choice due to sensitivity, efficiency, chemical inertness, safety or other concerns. Alternate carrier gasses, e.g. hydrogen or nitrogen, can be used in some instances. For a mass spectrometer detection based system, hydrogen decreases sensitivity for electron ionization (EI) and can cause dehydrohalogenation reactions in the ion source while nitrogen can result in charge exchange reactions, and is known to be less efficient as a carrier gas.

SUMMARY

A method of purging a gas chromatograph system according to the invention includes selecting between a first and a second mode. The first mode allows maximum helium conservation while the second mode allows minimum method impact e.g. retention times and detector responses.

When maximum helium conservation is selected, the inlet is supplied with an auxiliary gas that is non-helium; the pressure of the non-helium gas set to correspond to a given column flow. During an injection period, a coaxial helium flow is established around the end of the analytical capillary column, wherein the coaxial helium flow is less than the column flow. Following the injection period, a coaxial helium flow is established around the end of the analytical capillary column, wherein the coaxial helium flow is greater than the column flow.

When minimum method impact is selected, the inlet is supplied with helium and the pressure of the helium gas is set to correspond to a given column flow. During an injection period, a coaxial helium flow is established around the inlet end of an analytical capillary column, wherein the coaxial helium flow is less than the column flow. Following the injection period, a coaxial helium flow is established around the inlet end of an analytical column, wherein the coaxial helium flow is greater than the column flow. The inlet is then supplied with an auxiliary gas. The auxiliary gas may be hydrogen, nitrogen, or argon.

One embodiment for a gas chromatograph (GC) system according to the invention includes a helium gas source and a non-helium auxiliary gas source. A conduit surrounds the input end of an analytical column. A three-way valve receives one of an auxiliary gas and helium. An electronic pressure controller (EPC) connects to the three-way valve allowing both modes of operation described above. A separate on/off valve receives helium from a calibrated flow restrictor. The valve allows setting of two flow levels at a T-connector which interposes the injector and the analytical column. A gas chromatograph detector connects to the output of the analytical column. The injector may be operated in the split or splitless modes of operation. An optional heated precolumn interposes the output of the injector and the T connector.

Another embodiment for a gas chromatograph (GC) system according to the invention includes an injector having a threaded stem at a terminal end. The threaded stem includes a conduit having an input at an upper end of the threaded stem and an output at a lower end of the threaded stem. Within the injector body, there is an injection port liner, conduit within the injection port liner, an analytical column is encased by the conduit, a ferrule concentrically positioned around the conduit within the injection port liner, and a liner support and base are positioned adjacent the injector body and near the threaded stem such that the ferrule is compressed. A grooved gasket interposes the base and the threaded stem. Each face of the grooved gasket includes an annular groove. A via extends between the annular grooves. A valve communicates with the input end of a conduit which feeds helium to the base of the injector. Flow restrictors are utilized in order to establish one of two helium flow rates to the input end of the analytical column.

DETAILED DESCRIPTION

Figure 1:
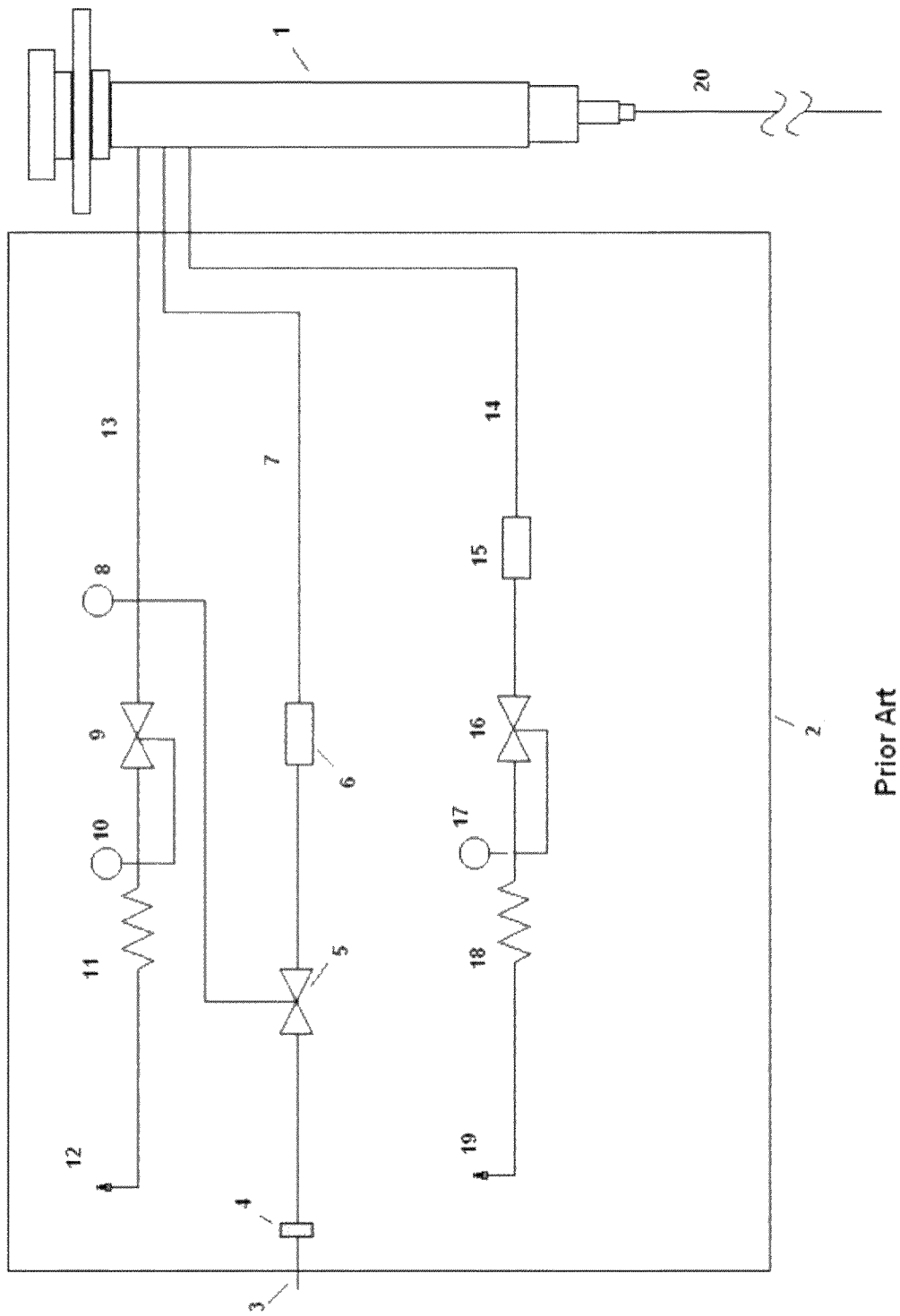
FIG. 1 shows a prior art Split/Splitless injection system.
Figure 2:
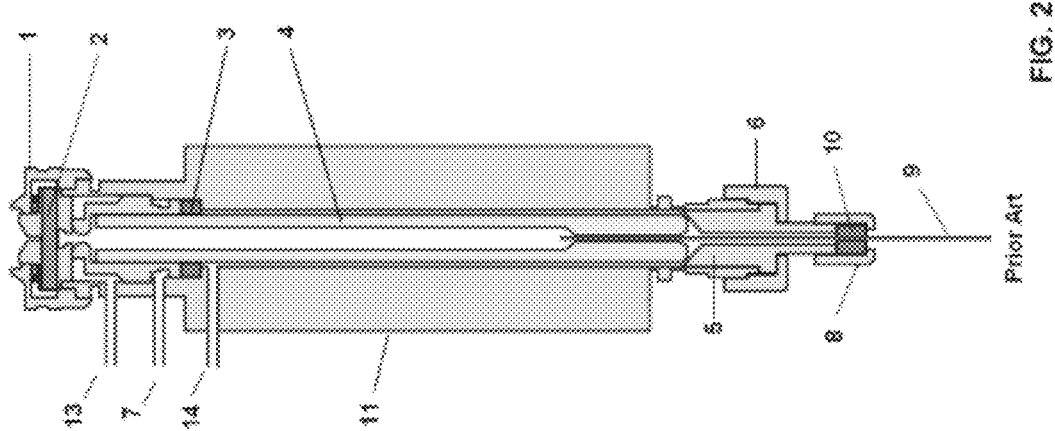
FIG. 2 shows a prior art Split/Splitless injector.
Figure 3:
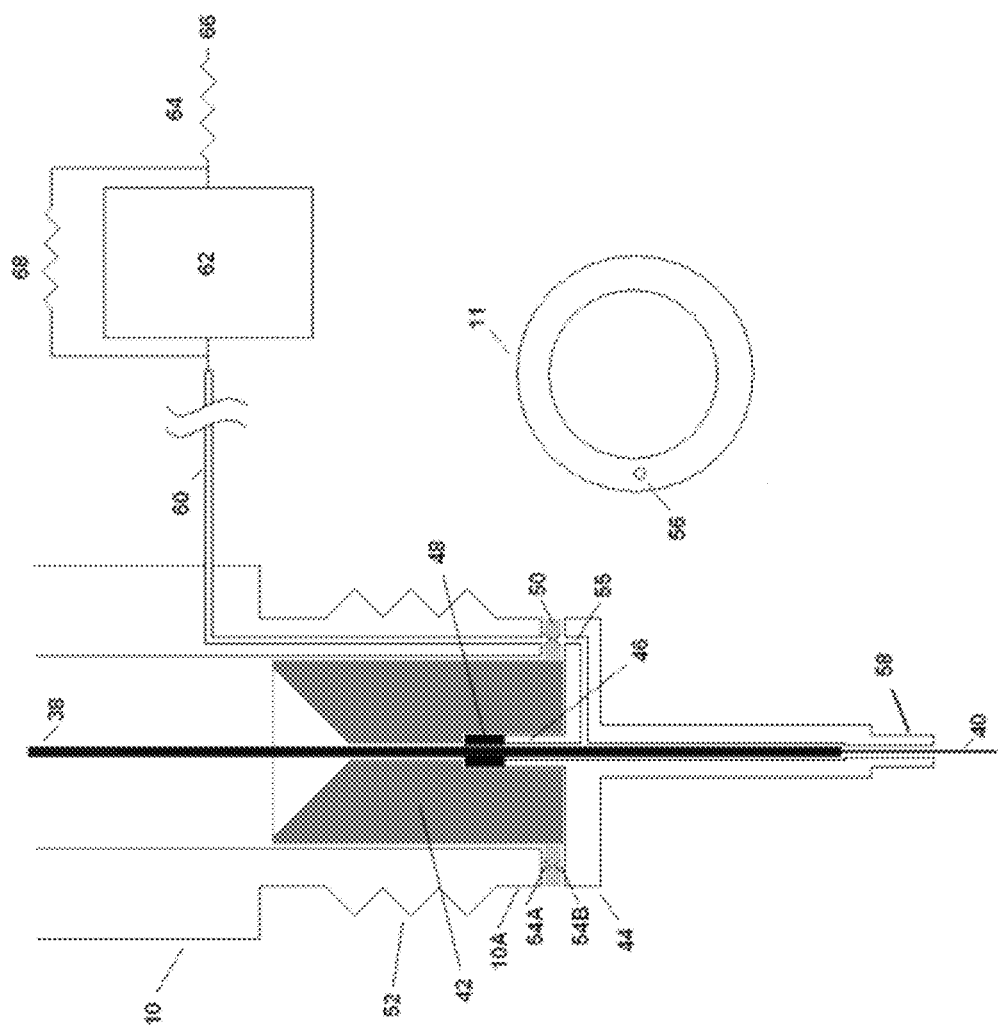
FIG. 3 shows the lower end of the Split/Splitless injector of FIG. 2 using a short narrow bore tube assembly of the present invention.

FIG. 3 illustrates an embodiment of the present invention. In this embodiment, the lower portion of an SSL injector is designed to allow helium gas to be selectively passed over the end of an analytical column. A gas other than helium is introduced to the injector in a conventional manner in order to pressurize the inlet and provide split flow and septum purge flow. The novel SSL injector body may be used in the system disclosed in FIG. 1.

The upper end of a conduit, e.g. short segment of deactivated fused silica tubing 38 is positioned within the confines of an injection port liner (not shown). Positioned within the tubing 38 is the analytical column 40. A liner support 42 and base 44 are screwed together at the threaded stem 46 to allow compression of the encapsulated graphite ferrule 48. This maintains a gas tight seal between the fused silica tubing 38 and the base 44. A soft metallic gasket 50 is positioned between the base 44 and terminal end of the injector 10A to create a seal between base 44 and the injector body 10. A retaining nut (not shown) secures the base 44 to the threaded portion 52 of injector body 10.

The short segment of fused silica tubing 38 is selected to have an internal diameter slightly larger than the outer diameter of the analytical column 40. For example, Megabore tubing of 0.53 mm ID is suitable for most analytical columns with internal diameters of 0.25 or 0.32 mm ID. Preferably the tubing has been deactivated and contains no stationary phase. This segment of tubing alternatively can be fabricated from glass lined stainless steel tubing, Silcosteel® tubing, or other suitably inert material.

In this illustrative example, the analytical column 40 extends preferably to within 1 cm of the uppermost end of the tubing 38. This allows locating the column entrance within the hot injector body, minimizes void volume effects and allows a sufficient back diffusion barrier to the auxiliary gas during analysis. The gasket 50 includes a pair of gas channels 54A, 54B in the form of an annular groove cut on each face of the metallic gasket 50. The gasket 50 shown in top view as 11 also includes a hole 56 located on the centerline of gasket 50 to create a fluid communication between the upper and lower groove channels 54A, 54B. The terminal end 58 of base 44 is threaded so that a retaining nut and ferrule (not shown for simplicity) can create a seal between the analytical column 40 and the base 44. A conduit 60 supplies a flow of helium to the upper groove channel 54A. The helium flows around the upper groove channel until it finds hole 56. It then passes through hole 56 into the lower groove channel 54B and into base 44 at entrance point 55. The base 44 allows the helium to flow downward around the outside of the fused silica tube 38 to sweep void volume then proceed upward into tube 38 and finally the injector interior after passing the input end of the analytical column 40. The flow established into the conduit 60 should be slightly higher than the calculated column flow delivered to column 40 following the injection period. To illustrate, 2 sccm of conduit flow could be used for calculated column flows of 1 sccm.

The flow delivered by the conduit 60 can be calculated using a mathematical model, or optimized empirically by adjusting the flow while monitoring the presence of auxiliary gas in the gas delivered to column 40. To illustrate, if nitrogen is the auxiliary gas delivered to the injector, and the detection system employs a mass spectrometer, the air/water spectrum can be monitored for the abundance of nitrogen in the column effluent. The helium flow can be adjusted accordingly to minimize consumption of helium while preventing undue back diffusion of nitrogen into the column.

During injection of a sample into the injector 10 of FIG. 3, the flow of helium into conduit 60 can be interrupted by closing the on/off valve 62 such that the delivered helium flow is reduced below the column flow. The auxiliary gas will then sweep sample components onto the analytical column 40. The flow is preferably reduced to a fraction of the column flow (rather than completely stopped) to a low value e.g. 0.05 sccm to help sweep void volumes, reduce peak tailing and prevent back diffusion of solvent vapors into the gas lines. Following the injection of the sample and sample transfer to the analytical column 40, the helium flow in conduit 60 is re-established by opening valve 62 so that the chromatographic process utilizes helium for the bulk of the analytical separation, while the auxiliary gas is used to purge the injector.

The embodiment of FIG. 3 uses hardware that may be removed from the system for maintenance and column positioning purposes while also allowing re-assembly which is immune to rotational positioning of the components. This provides significant ease-of-use.

The flow through a GC capillary column is typically established by setting an inlet pressure. The flow can be calculated and thereby controlled using prior knowledge of the gas viscosity, column dimensions and inlet and outlet pressures using the Poiseuille equation:

$$\frac{dV}{dT} = \frac{\pi r^4}{16\eta L}\left(\frac{(p_i^2 - p_o^2)}{p_o}\right) \qquad \text{Equation 1}$$

where:
$P_i$ inlet pressure
$P_o$ outlet pressure
L is the length of the column
$\eta$ is the viscosity of the gas
r is the column internal radius Since the inlet pressure is known, the conduit 60 can be connected to a solenoid valve 62 and a flow restrictor 64 of known dimensions external to the oven (not shown) proper, so that a pressure can be set upstream of it to affect a flow of helium across the input end of the analytical column. The low pressure drop which results in the ~1 cm length of 0.53 mm ID tubing near the end of the column ensures that the electronic pressure control is maintained resulting in nearly identical retention times as prior art methods. The electronic pressure control (EPC) functionality is not impaired by the operation of helium delivery to tube 38 of FIG. 3. The flow of helium to the column is maintained by the head pressure of the auxiliary gas in the injector, while the excess helium is simply diverted upward into the injector where it contributes to the bulk auxiliary gas purge. The inert nature of the deactivated fused silica tube 38 along with its short length ensure minimal surface activity and efficient sample transfer.

In this illustrative example, the conduit 60 may comprise a 304 stainless steel tube of 0.9 mm OD×0.5 mm ID×300 mm length. The conduit is attached to the hot injector body 10 and the opposite end attaches to an electrically actuated valve, e.g. low dead volume solenoid valve 62 and capillary restrictor 64 mounted external to the GC oven (not shown) at ambient temperature. The capillary restrictor 64 can have an internal diameter of 50 microns and be 500 mm in length. When restrictor 64 is pressurized to 100 psig at the inlet end 66, a helium flow of 2.8 sccm will be established when valve 62 is open and the injector is operated near ambient pressure. The injector 10 can be operated at higher pressures without undue drop in the restrictor flow, since the restrictor input is maintained at relatively high pressure. This simplifies the implementation of the hardware. Increasing the injector pressure to 30 psig for example will reduce the restrictor flow to 2.4 sccm allowing sufficient flow for both the analysis (1.0 sccm) and the prevention of significant back diffusion for small bore e.g. 0.25 mm ID analytical columns. In like manner, the restrictor 68 can have 15 microns ID and 200 mm in length to deliver a small 0.05 sccm residual purge when solenoid 62 is closed.

The flow of helium to the conduit 60 can be established by any means known in the current art including but not limited to programmable pressure and/or flow controllers, manual pneumatic controllers and regulators, secondary inlet pressure controllers e.g. (from a secondary GC inlet pneumatic module pressurizing a calibrated restrictor). Alternate configurations allowing helium flow to be used as the auxiliary gas during the injection period are also possible if configured, but will result in higher helium consumption.

Figure 4:
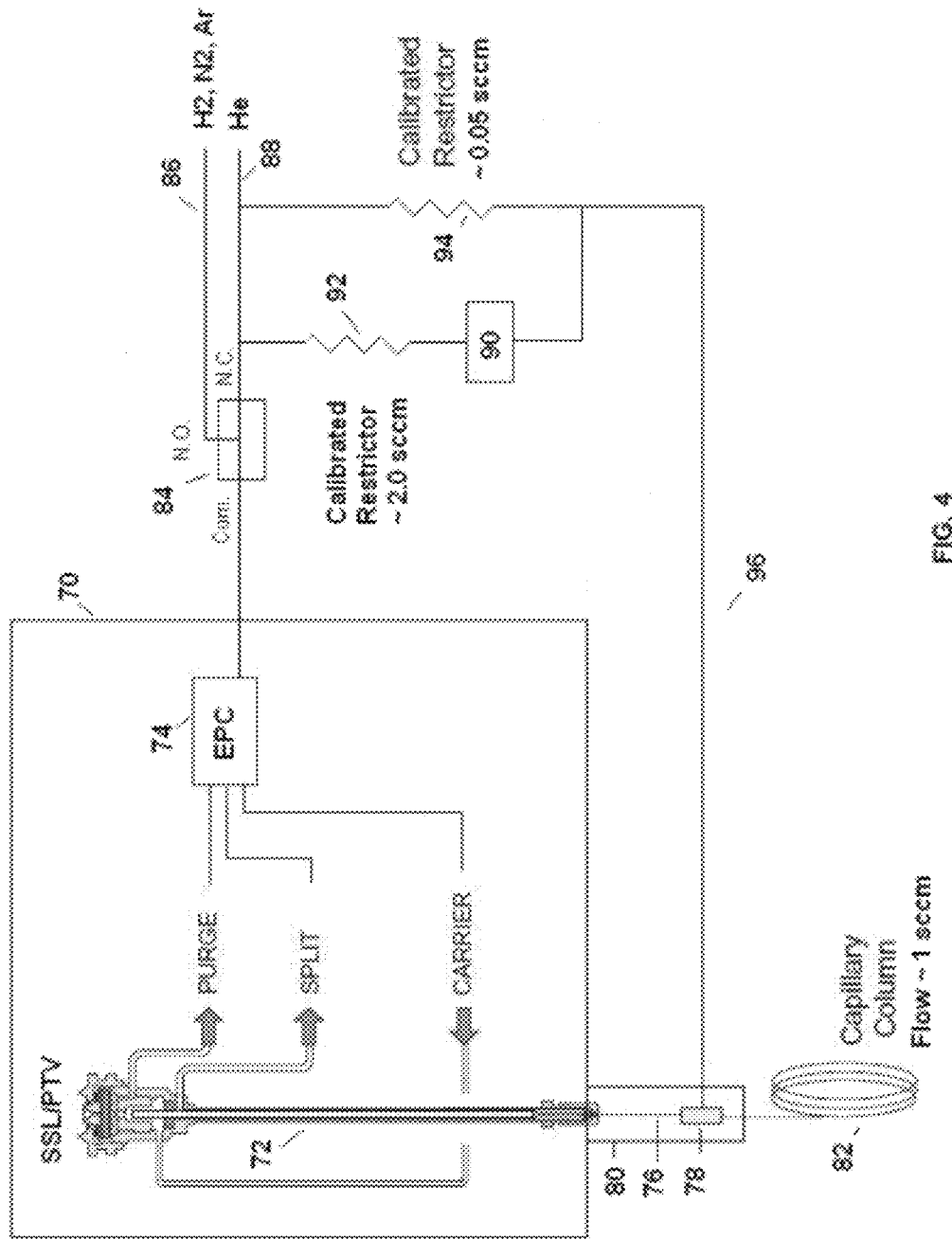
FIG. 4 illustrates another embodiment of the invention applied to an existing in-field gas chromatograph.

FIG. 4 illustrates an alternate embodiment of the present invention illustrating how it can be used on existing in-field chromatographs. An inlet system 70 comprising a PTV or SSL injector 72 and electronic flow controller 74 is outfitted with a short segment of pre-column 76 and low-dead-volume tee piece 78 housed in a small heated zone 80. The temperature control of heated zone 80 can be provided by an external controller or by an unused auxiliary heater channel as is often found on typical GC systems. The pre-column 76 is preferably as short as possible and comprises a few centimeter length of 0.53 mm ID fused silica tubing, steel clad fused silica tubing, glass lined stainless steel tubing etc. The inlet of analytical column 82 should pass through tee-piece 78 and terminate within the heated pre-column 76 preferably within one centimeter of the uppermost end. A 3-way solenoid selection valve 84 allows selection of one of an auxiliary gas at feed point 86 or a helium source delivered at feed point 88. The valve 84 allows (optionally) selection between helium and an auxiliary gas during the injection period. The three-way valve 84 can alternatively comprise a pair of on/off valves if superior isolation between helium and the auxiliary gas is desired. A second valve 90, of the on/off type receives a helium flow from feed point 88 via a capillary restrictor 92 set to a flow that is above the analytical column flow such as 2 sccm. The dimensions of the restrictors can be selected based on the input pressure of feed point 88 to establish a given flow range based on the pressure swing of injector 72. The actual flow can vary, e.g. 2-4 sccm without affecting performance. A capillary restrictor 94 is disposed in the flow path of conduit 96 for delivering a low purge flow for compensation of void volume effects. The flow delivered by the capillary restrictor 94 is lower than the analytical column flow and can be for purposes of illustration, 0.05 sccm. The second solenoid valve 90 can be actuated to deliver 2 sccm flow to the tee piece 78 during periods of run time or switched off during periods of injection, during cool down of the GC oven, or any non-run time period. Switching of the valve off during non-run time can reduce the helium consumption to nearly zero (0.05) for times when the instrumentation is not being used, utilizing instead the auxiliary gas for column flow. Activation of solenoid valves 84, 90 can be accomplished using the time events programming features of most modern day gas chromatographs.

Embodiments using nitrogen as the auxiliary gas are preferred. Nitrogen has a viscosity similar enough to helium to allow proper flow control of many existing septum purge and split vent hardware configurations on existing in-field chromatographs without modification. The similar viscosity also allows proper sample loading during injection. Large variations in viscosity relative to helium e.g. hydrogen, can be compensated for by using helium as the auxiliary gas during the injection period, or by altering the column head pressure during injection. Using a commercially available hydrogen or nitrogen gas generator along with embodiments of the present invention also allow for a large reduction in the number of high pressure cylinders and/or the frequency with which they need to be replaced. Argon can also be beneficially employed as a low cost inert gas delivered either via a high pressure cylinder or as a gas from the gas output valve of a liquid argon Dewar.

It is also envisioned that gas types not generally employed to pressurize GC inlets could also potentially be used. For example, liquefiable gasses such as carbon dioxide are low cost, and large gas volumes are available per cylinder since the gas exists in liquid form within the confines of the cylinder.

Figure 5:
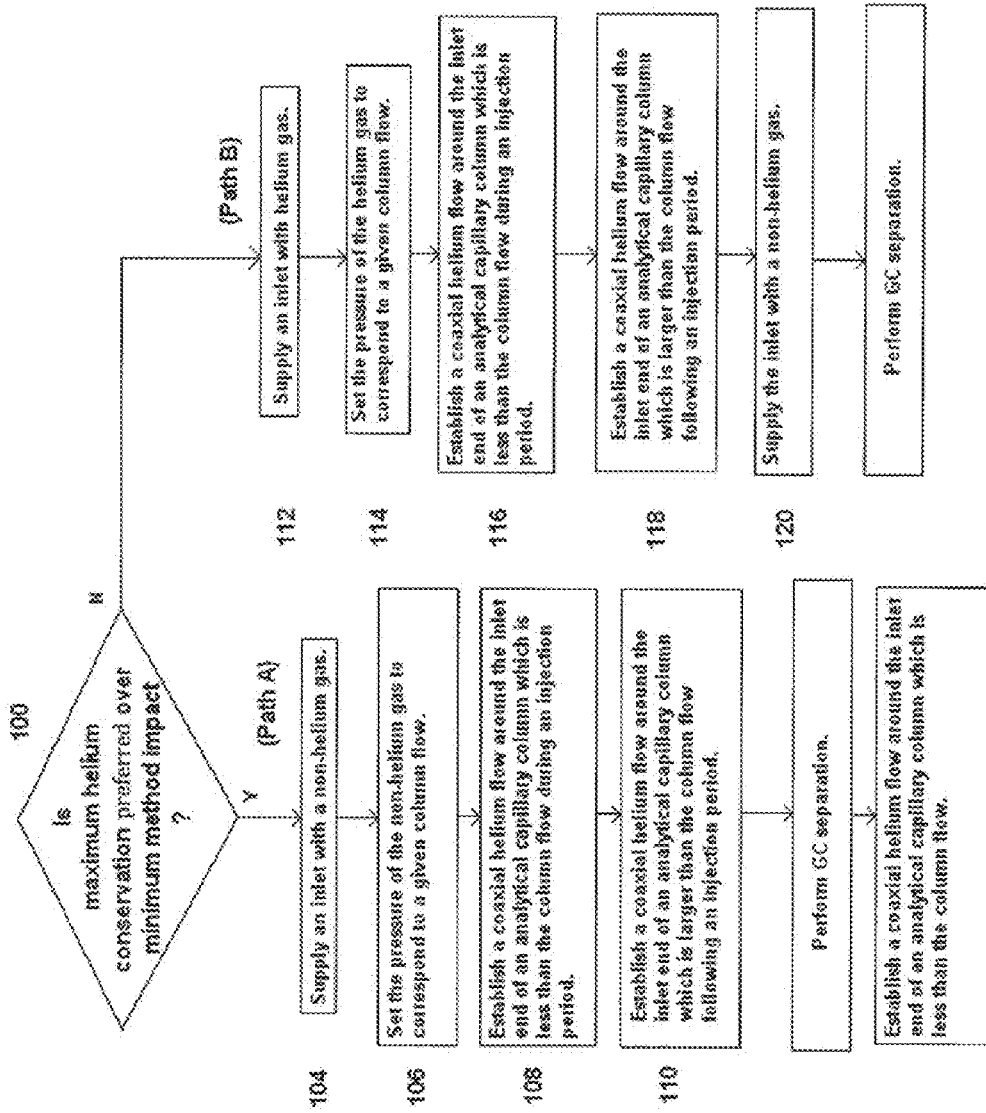
FIG. 5 illustrates a flow chart describing operation of the invention to conserve helium.
Figure 6:
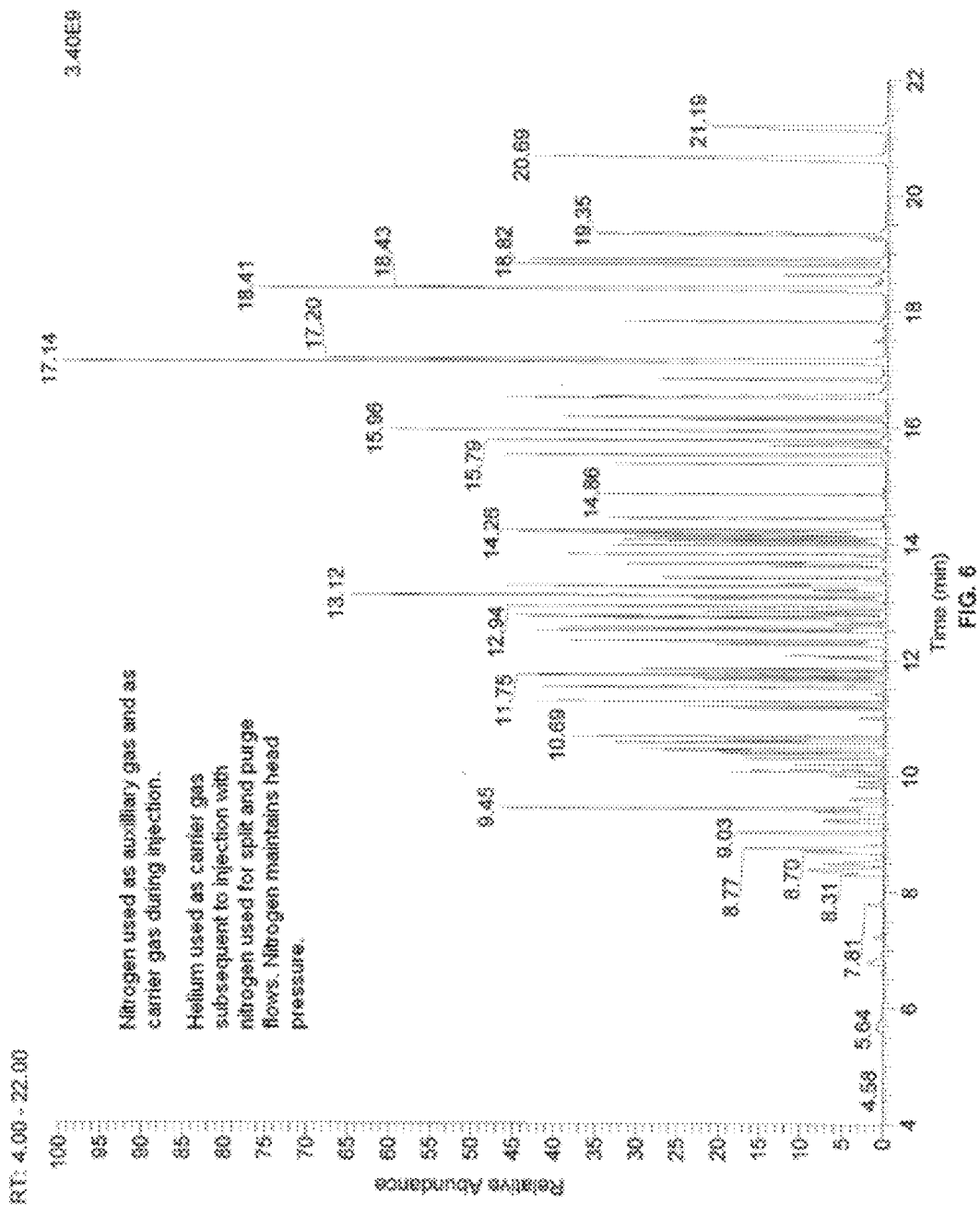
FIG. 6 illustrates splitless data gathered using nitrogen as auxiliary gas and helium as carrier gas.
Figure 7:
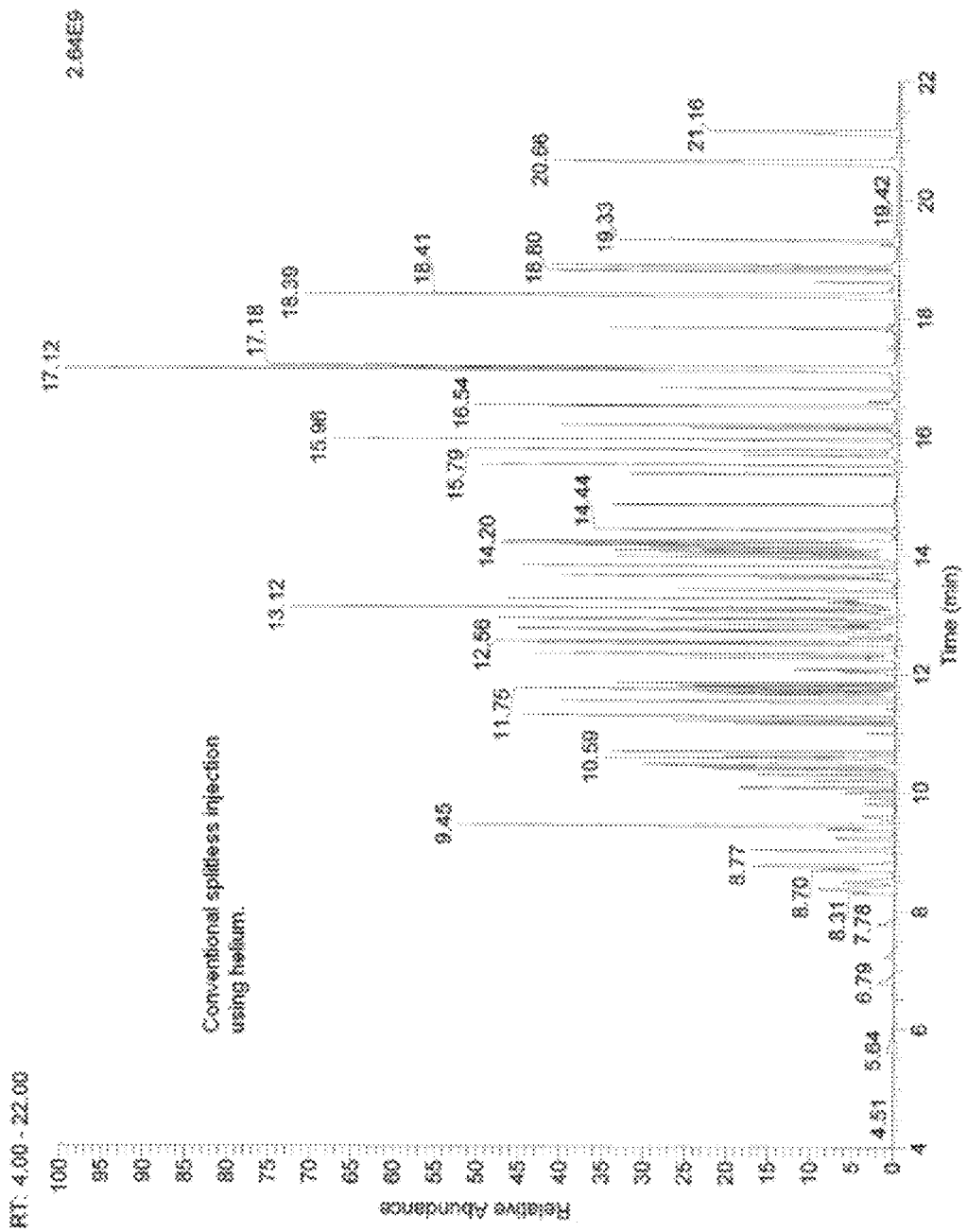
FIG. 7 illustrates splitless data gathered using helium only in conventional manner.

FIG. 5 shows a helium conservation flowchart for the operation of the gas chromatograph. In step 100, selection is made regarding the choice of gas present in the inlet during a sample injection. The user may decide between maximum helium conservation or minimum method impact e.g. preservation of retention times for early eluting components.

For maximum helium conservation the preferred choice is a non-helium gas such as nitrogen or argon. This sequence of events is shown in Path A. In step 104, the inlet is supplied with a non-helium gas. In step 106, the pressure of the non-helium gas is set to correspond to a given column flow. In step 108, during an injection period, a coaxial helium flow is established around the end of the analytical capillary column. The flow is less than the column flow. In step 110, after the injection period, a coaxial helium flow is established around the end of the analytical capillary column that is larger than the column flow.

For maximum inertness and preservation of retention times for early eluting components (minimum method effects), the sequence of events is shown in Path B. In step 112, the inlet is supplied with helium gas. In step 114, the pressure of the helium gas is set to correspond to a given column flow. In step 116, during an injection period, a coaxial helium flow around the inlet end of an analytical capillary column is established. This flow is less than the column flow. In step 118, after the injection period, a coaxial helium flow is established around the inlet end of an analytical column. The flow is larger than the column flow. In step 120, the inlet is supplied with a non-helium gas.

We claim:

1. A device for a gas chromatograph (GC) system comprising:
    an injector connected to a helium gas source and a non-helium gas source;
    wherein the non-helium gas source is configured to pressurize an input end of an analytical column and to deliver at least one of a split or purge gas flow; and
    a conduit assembly, including,
        a conduit surrounding the input end of the analytical column,
        a controller, connected to the conduit, having a first mode delivering a flow of helium which is less than the column flow during an injection period to effect a sample transfer to the column and a second mode delivering a flow of helium greater than the column flow following an injection period to prevent the non-helium gas from entering the analytical column.

2. A device as in claim 1, the controller including a pneumatic switch for temporarily switching the non-helium gas source to helium preceding an injection period, and switching back to the non-helium gas source following an injection period.

3. A device as in claim 1, wherein the controller is a secondary injector.

4. A device as in claim 1, the controller including an electronic pressure controller connected to a three-way valve receiving one of an auxiliary gas or helium;
    a secondary valve and calibrated restrictors for delivering two levels of helium flow to the conduit;
    a T connector interposes an injector and an analytical column, having a midpoint that connects to the conduit; and
    a gas chromatograph detector connects to the output of the analytical column.

5. The device of claim 4, wherein the gas chromatograph detector is a mass spectrometer.

6. The device of claim 1, wherein the injector is a split/splitless (SSL) injector.

7. The device of claim 1, wherein the injector is a programmed temperature vaporization injector (PTV).

8. The device of claim 1, wherein the auxiliary gas is selected from a group consisting of hydrogen, nitrogen, and argon.

9. The device of claim 7, further comprising a heated pre-column interposing the output of the programmable temperature vaporizing injector and the T connector.

10. The device of claim 1, the injector including:
    a removable 2-piece injector base having a threaded stem at a terminal end, the threaded stem including a conduit having an input at an upper end of the threaded stem and an output at a lower end of the threaded stem;
    above the removable injector base,
        an injection port liner;
        a conduit within the injection port liner;
        an analytical column positioned within the conduit;
        a ferrule concentrically positioned around the conduit, the 2-piece base threaded together such that the ferrule is compressed and;
        a grooved gasket interposing the base and injection port to effect fluid communication between the helium gas source and the base.

11. The device as in claim 10, wherein the analytical column is encased by the conduit.

12. The device of claim 10, the grooved gasket including:
    for each face of the gasket including an annular groove;
    a via within the annular grooves.

13. The device of claim 10, further including:
    a first valve in communication with the input end of the conduit;
    at least one capillary restrictor connected in series with the first valve; and
    the helium gas source in fluid communication with the at least one capillary restrictor, having a first mode directing the helium gas across the input end of the column at a flow rate larger than the flow rate of the column, having a second mode reducing the flow of the helium gas across the input end of the column to a value which is less than the flow of the column to effect a sample transfer to the column.

14. The device of claim 10, wherein the auxiliary gas is selected from a group consisting of hydrogen, nitrogen, and argon.

* * * * *